United States Patent
Chornenky et al.

(10) Patent No.: US 8,958,888 B2
(45) Date of Patent: *Feb. 17, 2015

(54) METHOD FOR RELAXING MUSCLE TENSION ON A TUBULAR ANATOMICAL STRUCTURE

(71) Applicant: AngioDynamics, Inc., Latham, NY (US)

(72) Inventors: Victor Chornenky, Minnetonka, MN (US); Ali Jaafar, Eden Prairie, MN (US)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/134,109

(22) Filed: Dec. 19, 2013

(65) Prior Publication Data

US 2014/0107643 A1  Apr. 17, 2014

Related U.S. Application Data

(60) Continuation of application No. 12/820,955, filed on Jun. 22, 2010, now Pat. No. 8,634,929, which is a continuation of application No. 11/347,965, filed on Feb. 6, 2006, now Pat. No. 7,765,010, which is a division of application No. 10/217,749, filed on Aug. 13, 2002, now Pat. No. 6,994,706.

(60) Provisional application No. 60/325,994, filed on Oct. 1, 2001, provisional application No. 60/311,792, filed on Aug. 13, 2001.

(51) Int. Cl.
*A61B 18/18* (2006.01)
*A61B 18/12* (2006.01)
*A61N 1/32* (2006.01)

(52) U.S. Cl.
CPC ............... *A61B 18/12* (2013.01); *A61N 1/325* (2013.01)
USPC .......................................... 607/101; 607/143

(58) Field of Classification Search
USPC ................................ 606/32–52; 607/101, 143
See application file for complete search history.

(56) References Cited

U.S. PATENT DOCUMENTS

| | | | | |
|---|---|---|---|---|
| 5,800,378 | A * | 9/1998 | Edwards et al. | 604/22 |
| 5,843,026 | A * | 12/1998 | Edwards et al. | 604/508 |
| 6,139,545 | A * | 10/2000 | Utley et al. | 606/34 |
| 6,405,732 | B1 * | 6/2002 | Edwards et al. | 128/898 |
| 6,463,331 | B1 * | 10/2002 | Edwards | 607/101 |
| 6,994,706 | B2 * | 2/2006 | Chornenky et al. | 606/41 |
| 7,130,697 | B2 * | 10/2006 | Chornenky et al. | 607/101 |
| 7,765,010 | B2 * | 7/2010 | Chornenky et al. | 607/101 |
| RE42,016 | E * | 12/2010 | Chornenky et al. | 607/101 |
| 2001/0044596 | A1 * | 11/2001 | Jaafar | 604/103.01 |
| 2001/0047167 | A1 * | 11/2001 | Heggeness | 606/41 |
| 2002/0138075 | A1 * | 9/2002 | Edwards et al. | 606/41 |
| 2005/0261672 | A1 * | 11/2005 | Deem et al. | 606/41 |
| 2006/0293713 | A1 * | 12/2006 | Rubinsky et al. | 607/2 |
| 2006/0293731 | A1 * | 12/2006 | Rubinsky et al. | 607/98 |

* cited by examiner

*Primary Examiner* — Linda Dvorak
*Assistant Examiner* — Jocelyn D Ram
(74) *Attorney, Agent, or Firm* — Peter J. Flora

(57) ABSTRACT

An apparatus and method for treatment of a tubular anatomical structure is disclosed. The method includes using an electrical signal to destroy elongated cells on the tubular anatomical structure. The apparatus may include one or more electrodes for creating an electric field, and a cooling system for carrying heat away from the electrode. The elongated cells can include nerve cells on the tubular anatomical structure.

16 Claims, 5 Drawing Sheets

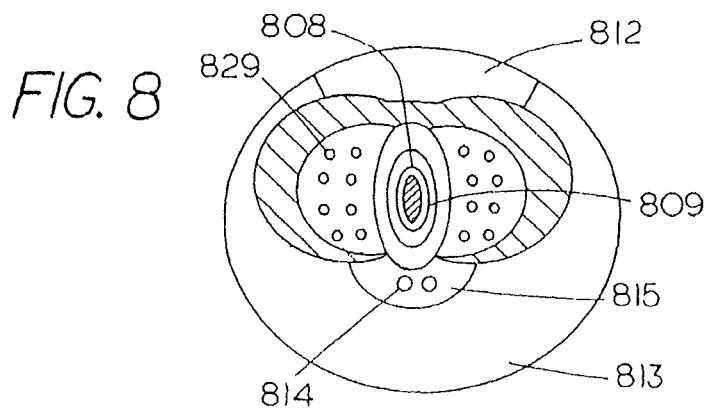
FIG. 8
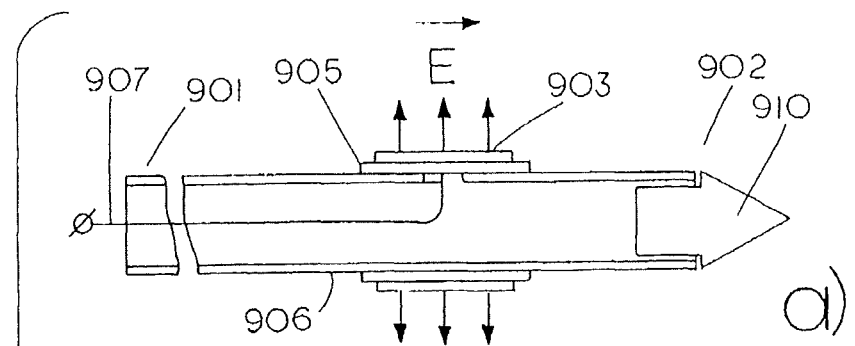
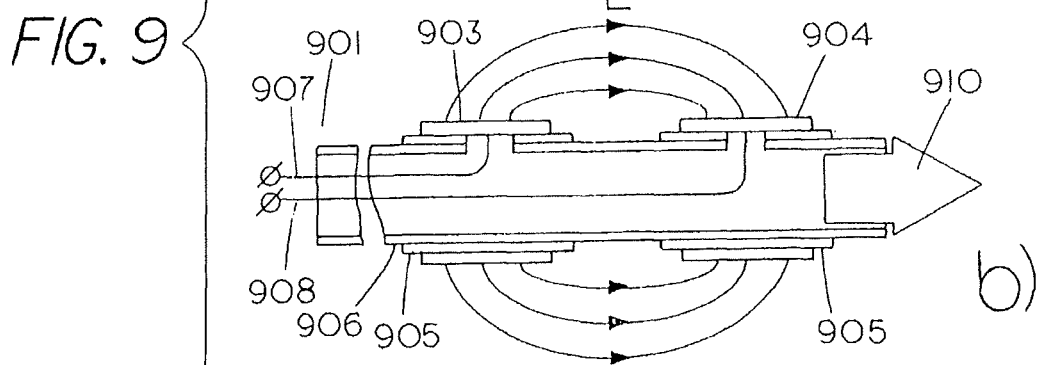
FIG. 9
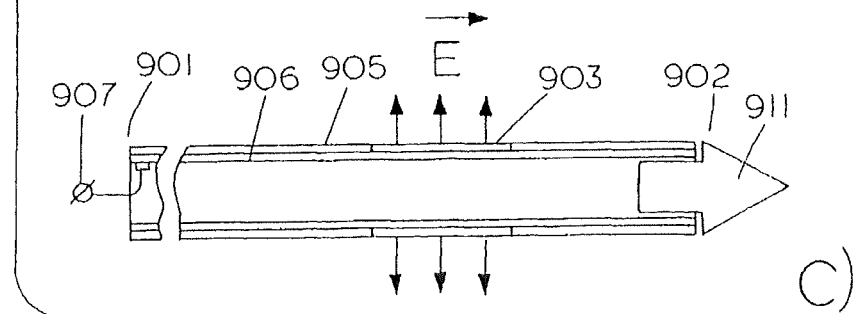

METHOD FOR RELAXING MUSCLE TENSION ON A TUBULAR ANATOMICAL STRUCTURE

CROSS REFERENCE TO RELATED APPLICATIONS

The present application is a continuation of U.S. patent application Ser. No. 12/820,955, filed Jun. 22, 2010, now U.S. Pat. No. 8,634,929, which is a continuation of U.S. patent application Ser. No. 11/347,965, now U.S. Pat. No. 7,765,010, filed Feb. 6, 2006, which is a division of U.S. patent application Ser. No. 10/217,749, now U.S. Pat. No. 6,994,706, filed Aug. 13, 2002, which claims priority to U.S. Provisional Application No. 60/311,792, filed Aug. 13, 2001 and to U.S. Provisional Application No. 60/325,994, filed Oct. 1, 2001, all of which are incorporated herein by reference.

FIELD OF INVENTION

The present invention relates generally to the therapeutic treatment of tissue and more particularly, to a method for treating muscle tension on a tubular anatomical structure of a patient.

DESCRIPTION OF THE RELATED ART a. Electroporation:

Biophysical phenomenon "electroporation" (EP) refers to the use of electric field pulses to induce microscopic aquatic pores—"electropores"—in the lipid cell membranes. Depending on the parameters of the electric pulses, electroporated cell can survive the pulsing or die. The cause of death of an electroporated cell is believed to be a chemical imbalance in the cell, resulted from the fluid communication with the extra cellular environment through the pores. The number and size of electropores depend on both, the amplitude of electric field pulse E and the pulse duration t. Electroporation is observed for pulse durations in the range from tens of microseconds to hundreds of milliseconds. For a given duration of a pulse and below a certain limit of the electric field amplitude, no pores are induced at all. This limit is different for different cells, particularly, for cells of different sizes. The smaller the size of a cell, the higher the electric field required to induce pores and thus the higher the limit is. Above the lower limit the number of pores and their effective diameter increases proportionally with both the amplitude E and duration t.

Until the upper limit of electroporation is achieved, the cells survive pulsing and restore their viability thereafter. Above the upper limit, the pore diameters and number become too large for a cell to survive. The irreversibly chemically imbalanced cell cannot repair itself by any spontaneous or biological process and dies. To kill a cell, a potential in the range of 2 to 4 V should be applied along the cell. The cell killing by electroporation is a probabilistic process. Increasing the number of applied pulses leads to increased probability of cell killing, approximately equal to the increase in the total duration of the electric pulse.

The survivability of electroporated cells depends significantly on their temperature. At higher temperature cells are more vulnerable, the amplitude and duration of the electric pulses required for cell killing are lower. This experimental fact is explained by two underlying phenomena: at higher temperatures cells are less stable biochemically because of more intense metabolism, and, secondly, at elevated temperatures the strength of lipid membranes decreases, which facilitates creating larger pores or irreversible rupture. At lower temperatures (10 to 20 degrees C.) cells are more resistant to electroporation and can survive two to three times higher voltages than that at the body temperature.

b. The Prostate Gland and Benign Prostatic Hyperplasia:

The prostate is a walnut-sized gland that forms part of the male reproductive system. The gland consists of several lobes, or regions, enclosed by a dense fibrous capsule. It is located between the bladder and the rectum and wraps around the urethra, the tube that carries urine out from the bladder through the penis. There are generally three glandular zones in a prostate gland: central, peripheral and transitional. The transitional zone is located right behind the place where the seminal vesicles are merging with urethra. This transitional zone tends to be predisposed to benign enlargement. The prostate gland is generally composed of smooth muscles and glandular epithelial tissue. The glandular epithelial tissue produces prostatic fluid. The smooth muscles contract during sexual climax and squeeze the prostatic fluid into the urethra as the sperm passes through the ejaculatory ducts and urethra. Prostatic fluid secreted by the prostate gland provides nutrition for ejaculated spermatozoids increasing their mobility and improves the spermatozoids chances for survival after ejaculation by making the environment in the vaginal canal less acidic.

The prostate reaches its normal size and weight (about 20 grams) soon after puberty. The size and weight of the prostate typically remain stable until the individual reaches his mid-forties. At this age, the prostate typically begins to enlarge through a process of excessive cell proliferation, called benign prostatic hyperplasia (BPH). This overgrowth can occur in both smooth muscle and glandular epithelial tissues and has been attributed to a number of different causes, including hormones and growth factors as well as generally to the aging process.

Benign prostate hyperplasia can cause distressing urination symptoms. As the disease progresses the dense capsule surrounding the enlarging prostate prevents it from further expansion outward and forces the prostate to press against the urethra, partially obstructing the urine flow. The tension in the smooth muscles of the prostate also increases which causes further compression of the urethra and reduction of the urine flow. Some symptoms of BPH stem from the gradual loss of bladder function leading to an incomplete emptying of the bladder. The symptoms can include straining to urinate, a weak or intermittent stream, an increased frequency of urination, pain during urination, and incontinence—the involuntary loss of urine following an uncontrollable sense of urgency. These symptoms alone can negatively affect the quality of life of effected men. Left untreated, BPH can cause even more severe complications, such as urinary tract infection, acute urinary retention, and uremia.

Before age 40, only 10% of men have benign prostatic hyperplasia; but by age 80, about 80% have signs of this condition. Benign prostatic hyperplasia is the most common non-cancerous form of cell growth in men. About 14 million men in US have BPH, and about 375,000 new patients are diagnosed every year.

For many years, researchers have tried to find medications to shrink the prostate or at least stop its growth. Between 1992 and 1997, the FDA approved four drugs: finasteride, terazosin, tamsulosin, and doxazosin for treatment of BPH.

Finasteride (Proscar) inhibits production of hormone DHT. DHT is one of the hormones that have been found to be involved in prostate enlargement. Treatment with Finasteride has been shown to actually shrink the prostate in some men.

Terazosin (Hytrin), doxazosin (Cardura), and tamsulosin belong to the class of drugs known as alpha-blockers. Alpha-blockers act by relaxing the smooth muscle of the prostate and bladder to improve urine flow and reduce bladder outlet obstruction. In men with severe symptoms, though, these medications are not curative. They can delay but not prevent the eventual need for surgery.

Regardless of the efficacy of any drug treatment, the long term exposure to xenobiotic compounds may produce additional unwanted side effects that are not realized until years after treatment. Accordingly, a need exists for an apparatus and method for the treatment of BPH that does not require the introduction of xenobiotic compounds.

For men with the most severe symptoms, surgery is generally considered to be the best long-term solution. There are several surgical procedures that have been developed for relieving symptoms of BPH. However, all of them are very morbid, require a long hospital stay, generally require the use of general anesthesia, suffer from significant side effects, and have possible complications.

In recent years, a number of procedures have been introduced that are less invasive than surgery. One such procedure is the transurethral microwave thermal therapy described in U.S. Pat. No. 5,575,811. In transurethral microwave thermal therapy, a Foley-type catheter containing a microwave antenna is placed within the urethra. The microwave antenna positioned adjacent to the transitional zone of the prostate, where BPH is located, allows selective heating of the prostate. Maintaining the temperature above 45.degree. C. during about one hour session leads to necrosis of the tissues and subsequent reabsorption of necrotic tissue by the body.

Another recently developed non-invasive technique is transurethral needle ablation (TUNA). TUNA is described in U.S. Pat. No. 6,241,702. TUNA uses low level radio frequency (RF) energy to heat the prostate. Using TUNA, two separate needles are inserted into prostate through the urethra. Several watts of RF energy is applied to each needle to cause thermal necrosis of the prostate cells around the needles. Application of this treatment to several sites of the prostate typically results in sufficient necrosis to relieve symptoms of the BPH.

While generally successful, the microwave and RF therapies are relatively long procedures. Also, because of the poor temperature control of the heated volume, the volume of removed tissue is often not sufficient for the long term relief of the symptoms and/or the healthy tissue of the urethra is damaged. A damaged urethra is capable of restoring itself, but the healing is a long morbid process accompanied by sloughing of the necrotic tissue into urethra and excreting it during urination.

Therefore, a need exists for a minimally invasive therapy for treatment of BPH that requires shorter treatment times and is less morbid than existing therapies.

SUMMARY OF THE INVENTION

The present invention satisfies the above-listed needs and provides additional improvements and advantages that will be recognized by those skilled in the art upon review of the following description and figures.

The object of the present invention is to provide a treatment that causes necrosis of BPH in a shorter period of time than that of the existing transurethral thermal therapies.

Another object of the present invention is to destroy nerves causing tension in the fibro-muscular tissue and thus achieve relaxation of the muscles contracting the urethra.

Another object of the present invention is to decrease morbidity of the treatment.

Another object of the present invention is to improve control of the volume in the prostate where necrosis occurs, avoid sloughing of the necrotic tissue through the urethra and decrease the damage to the urethra itself.

A shorter treatment time is achieved by applying to the tumorous tissue multiple high voltage pulses that cause necrosis of BPH by electroporation.

In one aspect, the present invention provides a method for treating a tubular anatomical structure. In certain embodiments, the method includes the steps of advancing into the tubular anatomical structure a catheter having at least one electrode, and applying, using the advanced electrode, an electrical signal in an amount sufficient to destroy elongate nerve cells.

In another aspect, the present invention provides a method for treating a tubular anatomical structure including advancing into the tubular anatomical structure a catheter having at least one electrode, applying, using the advanced electrode, an electrical signal in an amount sufficient to destroy elongate nerve cells, where the step of applying includes applying the electrical signal in a direction which is substantially radial to the tubular anatomical structure.

In yet another aspect, the present invention provides a method for treating a tubular anatomical structure, the method including advancing into the tubular anatomical structure a catheter having at least one electrode, positioning the electrode of the advanced catheter near a target area containing elongate nerve cells, applying, using the positioned electrode, a plurality of electrical pulses to cause an electric field in an amount sufficient to destroy the elongate nerve cells in the target area, where the step of applying includes applying a plurality of electrical pulses to cause the electric field in a direction substantially along the length of the elongate nerve cells.

In yet another aspect, the present invention provides a method for treating a tubular anatomical structure, the method including advancing into the tubular anatomical structure a catheter having at least one electrode, positioning the electrode of the advanced catheter near target area containing elongate nerve cells, applying, using the positioned electrode, a plurality of electrical pulses to cause an electric field in an amount sufficient to destroy the elongate nerve cells in the target area, wherein the step of applying includes applying the electrical pulses to cause the electric field in a direction which is substantially radial to the tubular anatomical structure.

The present invention, as well as its various features and advantages, will become evident to those skilled in the art when the following description of the invention is read in conjunction with the accompanying drawings as briefly described below and the appended claims. Throughout the drawings, like numerals refer to similar or identical parts.

BRIEF DESCRIPTION OF THE DRAWINGS

FIG. 8 illustrates a cross-section of the prostate with electrodes of the urethra-perineal applicator in place; and.

FIG. 9 illustrates a schematic drawing of needles used in different versions of the apparatus for treatment of BPH in accordance with the present invention.

Figure 1:
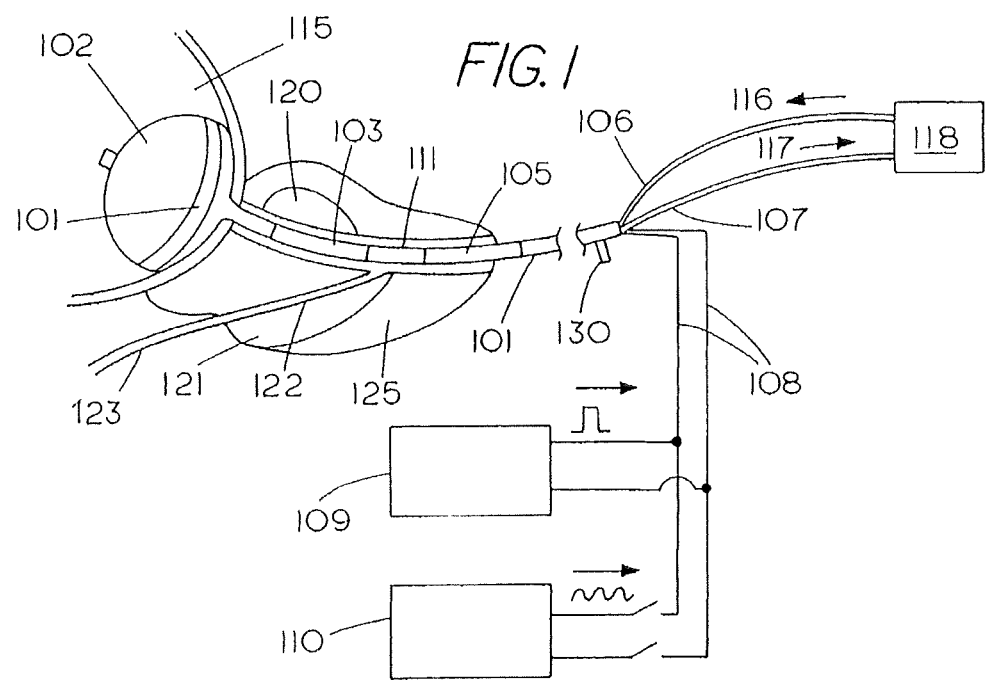
FIG. 1 is a schematic illustration of an embodiment of an apparatus for treatment of BPH in accordance with the present invention.

All figures are drawn for ease of explanation of the basic teachings of the present invention only; the extensions of the figures with respect to number, position, relationship and dimensions of the parts to form the preferred embodiment will be explained or will be evident to those skilled in the art after the following description has been read and understood. Further, the exact dimensions and dimensional proportions to conform to specific force, weight, strength, and similar requirements will likewise be evident to those skilled in the art after the following description has been read and understood.

Where used in various figures or on multiple occasions within the same figures, the same numerals generally designate the same or similar parts or features. Furthermore, when the terms "vertical," "horizontal," "top," "bottom," "right," "left," "forward," "rear," "first," "second," "inside," "outside," and similar terms are used, the terms should be understood to reference only the structure shown in the drawings as it would generally appear to a person viewing the drawings and utilized only to facilitate describing the illustrated embodiment.

DETAILED DESCRIPTION OF THE INVENTION

In one aspect, the current invention in part stems from recognition of the fact that the effect of electroporation on tissue can be modulated by selecting a specific direction relatively to a cell for application of a pulsed electric field. For elongated cells similar to muscle fibers the length-to-width ratio can be as high as 20 to 30. For the nerve cells this ratio can be even higher. The vulnerability of cells to electroporation is different for different directions of the applied field. It depends on the size of a cell in the direction of the applied field. In other words, elongated cells can be killed with significantly lower electric field if the field is applied along the cells. If the field is applied across the cell, the cell is capable of surviving much higher amplitudes of the electric field.

In the current invention relief of symptoms is achieved by electroporation treatment, which is used to create a necrotic zone in the BPH tissue around the urethra. Necessary control of the volume of the necrotic area, its shape and location relatively to the healthy tissues of the prostate and urethra can be provided by a system of electrodes generating electric field in the area of the benign enlargement of the prostate. Application of multiple electrical pulses with appropriate voltage and duration leads to necrosis of prostatic tissues around the urethra.

Anatomically, predominant direction of fibers in the fibro-muscular glandular tissue of BPH is radial to the urethra. In the present invention the preferred direction of applied electric field is also radial to the urethra, coinciding with the direction of fibers. Application of the electroporating pulses along the muscular fibers and nerves that anatomically follow them selectively kills both types of fibers. Thus two intermediate goals of the present therapy become achieved: first, a significant volume of necrotic BPH tissue around the urethra is created; second, the nerves causing elevation in tension of the muscle fibers are destroyed. Removal of the necrotic tissue by macrophages decreases the total volume of BPH and reduces pressure on the urethra. Destruction of the nerves results in relaxation of the prostate. Subsequently, both effects contribute to the improvement of the urethra and bladder functions after treatment.

To apply a pulsed electric field to the BPH region in the transition zone of the prostate, a set of electrodes is placed into the urethra (and the bladder) on the urethral catheter. In other embodiments of the invention, external electrodes are utilized or needle-type electrodes may be introduced into the volume of BPH tissue. The electrodes are electrically connected to a generator producing high voltage pulses, the amplitude and duration of which are selected to provide electric field in the prostatic tissue exceeding the upper electroporation limit for the fibro-muscular cells. Duration of pulses may be selected from the range of 10 microseconds to 500 milliseconds. The amplitude and number of pulses are preselected to cause necrosis of the BPH cells, mainly muscle cells and nerves.

Sphincters, located on the urethra anterior and posterior to the prostate gland, consist of smooth muscle cells wrapped circumferentially around the urethra. They control shutting down the flow of urine from the bladder and should be preserved during the treatment. Radial electric field applied to the prostate is transversal to the sphincter muscle fibers to which they are relatively resistant. However, to ensure that electroporation injury to the sphincters is avoided, the electrode in the urethra between the sphincters should not be positioned too close to them. For the same reason the amplitude of the electric field during treatment should be selected not to exceed the upper electroporation limit of the sphincter muscles in the transversal direction.

In another aspect, the present invention provides an apparatus and method for treatment of the prostate. The invention is generally described in the context of an apparatus and method for the treatment of BPH as a specific example for illustrative purposes only. Upon review of the following description and figures, those skilled in the art will understand that an apparatus in accordance with the present invention may be used for a wide variety of indications.

An apparatus for treatment of the prostate in accordance with the present invention is shown in FIG. 1. A Foley type urethral catheter 101 includes balloon 102 at its distal end. Urethral catheter 101 is introduced into the urethra 111 (411 in FIG. 4) and balloon 102 positioned within the bladder 115. As illustrated, transition zone 120 of the prostate is being treated for BPH. Anatomically, central zone 121, peripheral zone 125 seminal vesicle 123, and ejaculatory duct 122, are illustrated. Ejaculatory duct 122 delivers the sperm into the prostatic urethra during sexual climax. The catheter can include an electrode 103 adjacent to the prostate in the transition zone 120, and an electrode 104, placed into the bladder distally to the urethra or outside of the urethra on the skin (not shown) of the patient.

An implementation of the present invention having three electrodes is shown in FIG. 1: electrode 104 is in the bladder, electrode 103 is adjacent to the transition zone, electrode 105 can be placed proximally to the electrode 103 in the urethra. Placing more than two electrodes allows achieving better concentration of electric field on affected region of the prostate in the transition zone. A port 106 may be provided in the proximal end of the urethral catheter serving as an inlet for the coolant intended to cool the urethra as the prostate is heated. In one aspect, the prostate may be heated using RF. Therefore, an radio frequency (RF) generator 110 is illustrated for exemplary purposes. In this embodiment, a port 107 can also be provided to serve as an outlet for the coolant carrying the heat from the electrodes 103 and 105 via a flexible tube 117 to the coolant system 118. Wires 108 (408 in FIG. 4) can be provided to connect electrodes 103, 104, 105 with a generator 109, sending electroporation pulses to BPH. For purposes of electroporation, generator 109 is typically configured to provide high voltage. During treatment, the urethra may be cooled by a cooling system 118. Outlet 130 is a channel, fluidly connected to the balloon 102 and serving for its inflation in the bladder 115.

Figure 2:
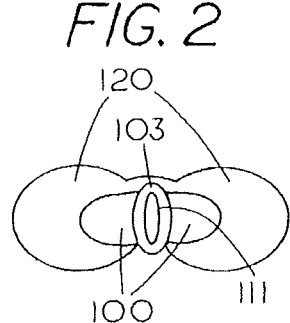
FIG. 2 illustrates a cross-section of the prostate with the urethral catheter in place.

In FIG. 2 a cross-section of an embodiment of the urethral catheter 101 inserted through a prostate is illustrated. Number 100 corresponds to the transition zone of the prostate 120 effected by BPH. Electrode 103 is positioned in the prostatic urethra 111.

Figure 3:
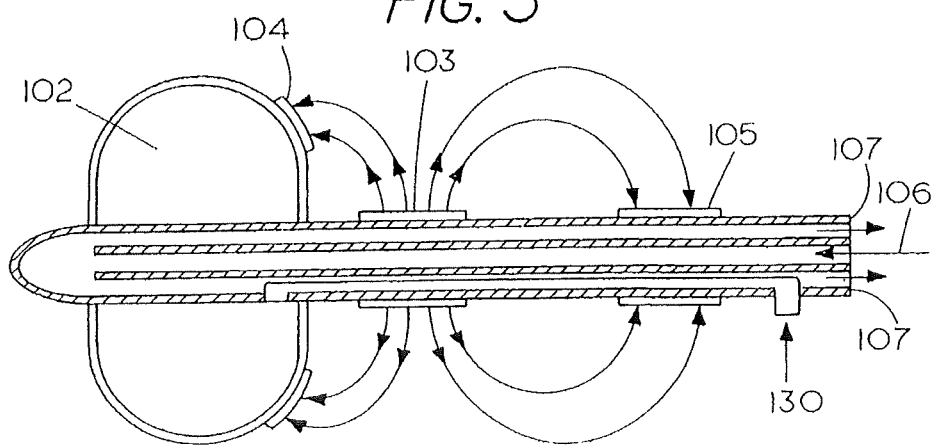
FIG. 3 illustrates a longitudinal section of the urethral catheter.
Figure 4:
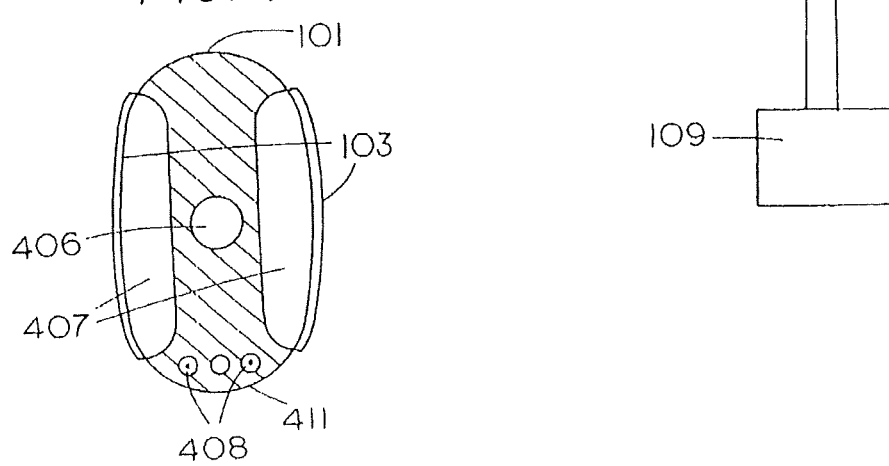
FIG. 4 is an enlarged view of a cross-section of the urethral catheter.

FIG. 3 and FIG. 4 show a longitudinal-section and a cross-section of an embodiment of the urethral catheter 101. Number 103 corresponds to the urethral electrode, 406 is the channel in the catheter, fluidly connected to the inlet 106 at the proximal end of the catheter and accepting the coolant liquid from the pump, not shown in the figure. Number 407 is designated for two channels in the catheter in which the coolant moves back to the proximal end, where through the outlet 107 it is returned to the cooling system.

Figure 5:
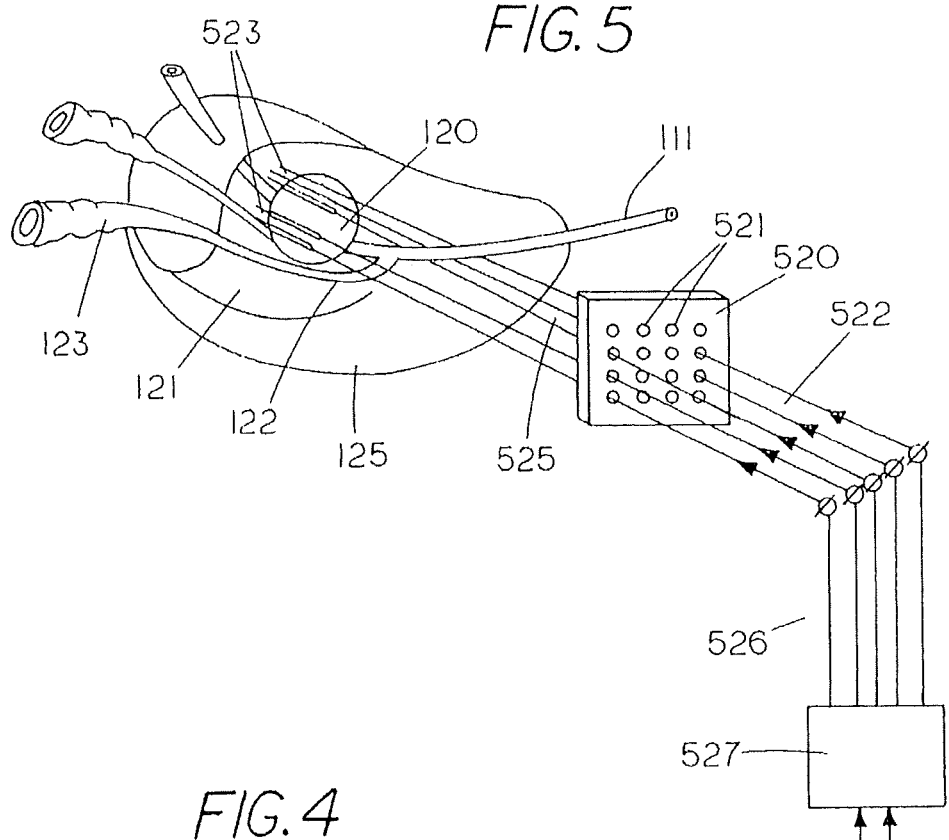
FIG. 5 illustrates an embodiment of an apparatus for treatment of BPH with a perineal needle template.

Another apparatus for implementing the method in accordance with the present invention employing a perineal needle template for placement of electrodes into BPH is depicted in the FIG. 5. Here 520 is a needle perineal template with holes 521 for directing needles having proximal end 522, distal ends 523 and elongated part 525. The proximal ends are electrically connected to multi electrode connector 526, leading to a switch board circuit 527, which, in turn, is connected to the output of the high voltage pulse generator 109.

Figure 6:
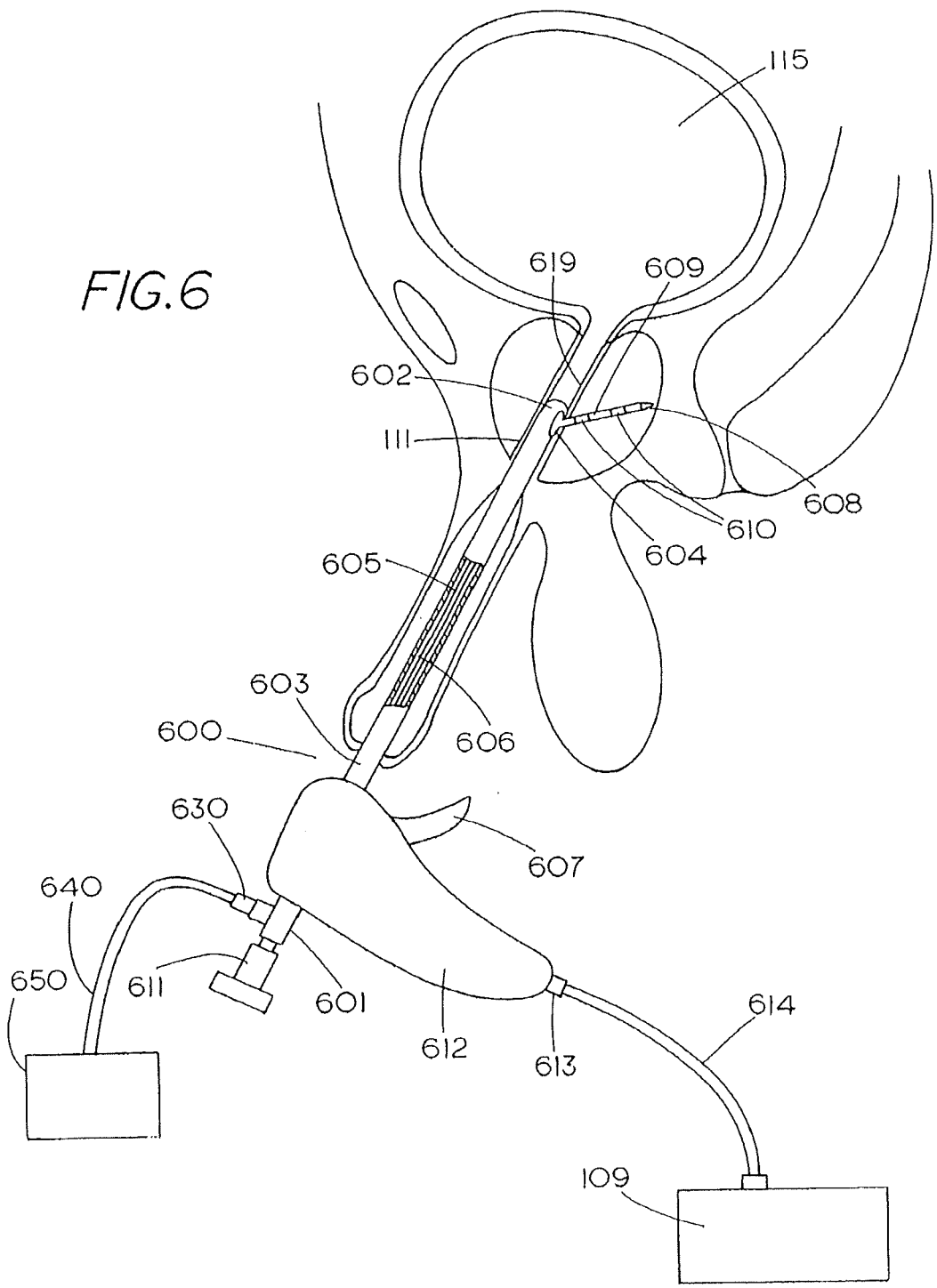
FIG. 6 illustrates an embodiment of an apparatus for treatment of BPH with a urethral probe having a two-electrode needle.

An apparatus for treatment of BPH by electroporation employing a urethral probe—an applicator for placement of electrodes into the prostate via urethra, is shown in FIG. 6. The apparatus comprises a urethral probe 600 having a proximal end 601, elongated member 603 and a distal end 602. The elongated member 603 has a passageway 606 extending from the proximal end of the probe 601 to its distal end 602 and ending at a side port 604 of the probe 601. In the passageway at the proximal end of the probe, an endoscope 611 is introduced. The endoscope has a wide-angle view and allows one to visualize the urethra at the distal end of the probe and thus provides visual control during manipulation of the probe. The endoscope has a fiber optic port 630 secured to a cable 640 connected to a light source 650. The light source 650 provides necessary illumination of the urethra beyond the distal end of the probe. Probe 600 is attached to a control handle piece 612. A flexible needle 605 inside passageway 606 extends throughout its length from the proximal end where it is engaged with a finger 607 via a mechanism adapted for advancement or retraction of the needle along the probe. Being advanced forward, the needle 605 bends at the distal end 602 of the probe 601 and comes out from the side port 604 under an angle close to 90 degrees to the urethra. Control handle piece 612 is used for manipulation of angular and longitudinal positions of the probe in the urethra and placement of the distal end 602 of the probe 601 into several locations along the transition zone of the prostate. The needle has a sharp tip 608 which easily penetrates through the urethra wall 619. Electrodes 610 on the distal part 609 of the needle thus placed into the volume of the BPH. The electrodes are spatially and electrically separated and, being pulsed by a high voltage, are capable of creating a substantial radial electric field along the muscle fibers of the BPH. Two wires leading from the electrodes 610 are extended through the needle 605 to its proximal end and further inside the handle 612 to the connector 613, where they are connected to the cable 614. The cable 614 is connected to the generator 109.

Under endoscopic guidance the probe is introduced by a physician into the patient's urethra with the distal end of the probe positioned inside the prostate. The needle of the probe is advanced into the BPH tissue surrounding the urethra and multiple HV pulses are applied. The end point of the electroporation therapy is a significant and stable drop in the electrical resistance of the treated volume. The resistance drop indicates profound electroporation damage to the fibro muscular cells, which later on leads to their necrosis. Overall treatment of one site takes about 10 pulses and several seconds to several tens of seconds in time depending on the repetition rate of the pulse generator.

Figure 7:
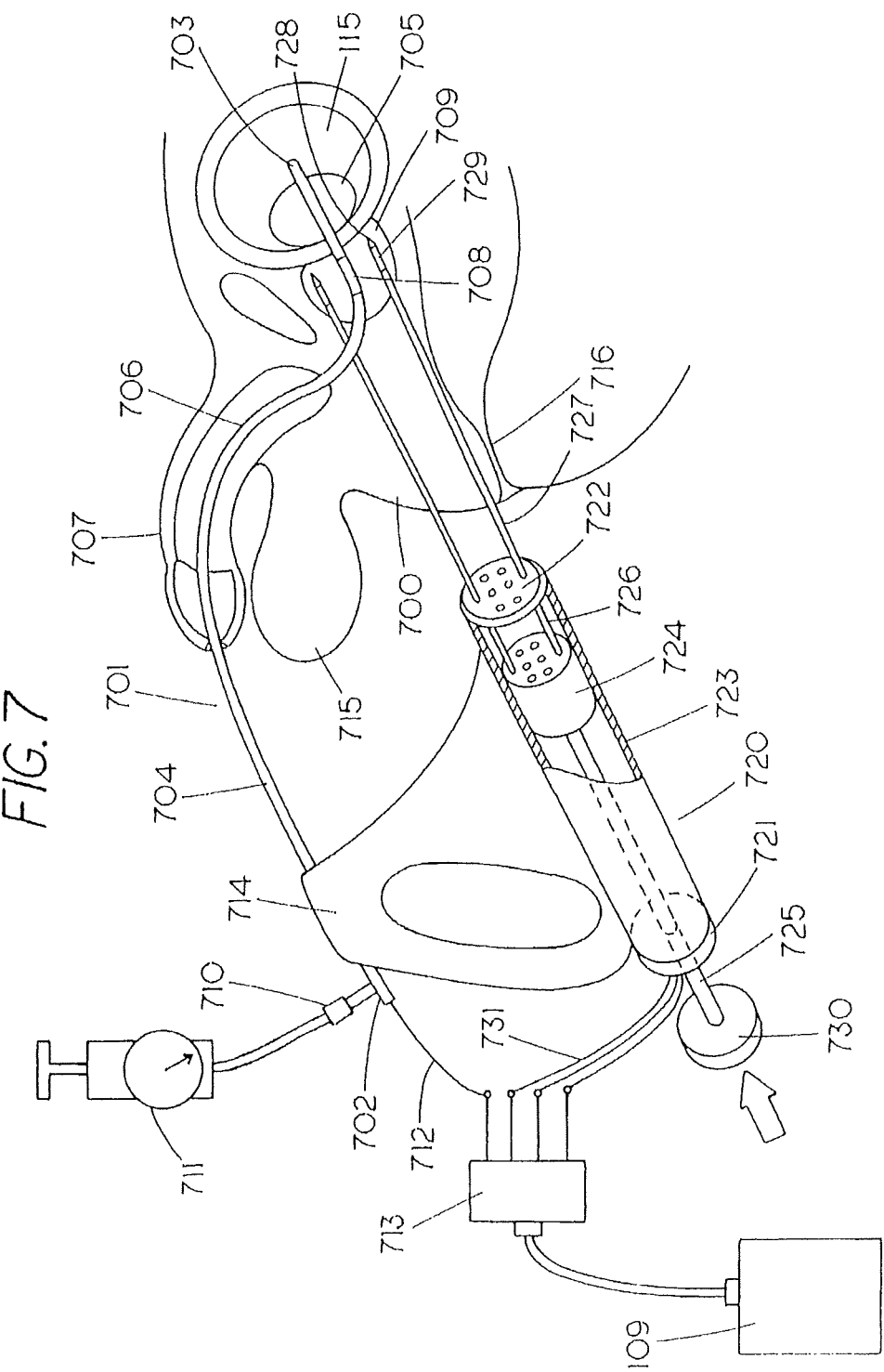
FIG. 7 illustrates a version of the apparatus in accordance with the present invention for treatment of BPH with a urethra-perineal applicator.

Another implementation of the current invention is shown in the FIG. 7. In this version of the apparatus, the needle electrodes are delivered to the prostate by a urethra-perineal apparatus. This apparatus is a combination of a urethral probe carrying a central electrode in the prostatic segment of the urethra and a cartridge of needle electrodes placed into the body of the prostate via a perineal approach. The urethral probe 701 is made of a rigid material, preferably metal, and has a proximal end 702, a distal end 703 and an elongated member 704. The distal end of the probe 703 is terminated with a balloon 705 adapted for inflation in the patient bladder 115. During treatment, the probe is introduced into urethra 706 of penis 707 and balloon 705 is inflated. Inflated balloon 705 anchors the probe longitudinally relatively to the bladder and prostate. The length of the urethral electrode and the distance between the electrode and the balloon are selected in such a way that the electrode is placed precisely adjacent to the BPH in the transition zone of the prostate 709. Balloon 705 via a channel inside the probe 701 fluidly communicates with inflation port 710 connected to a syringe 711 actually inflating the balloon. The urethral electrode 708 electrically connected to a wire 712 coming out of the distal end of the probe 702 to switching board circuit 713 whose function is the distribution of the high voltage pulses received from the generator 109 between electrodes placed into prostate during electroporation treatment. The urethral probe 701 is attached to a handle piece 714 used for longitudinal and angular manipulation of the probe. A cartridge 720 used for placement of needle electrodes into prostate via perineal approach is secured at the opposite side of the handle piece 714. The cartridge 720 has a proximal cap 721, a distal cap 722 and a cylinder 723 between them. A piston 724 secured at the end of a plunger 725 slides inside the cylinder 723 between two extreme positions, a proximal and a distal one. In the proximal position the needles are hidden in the cylinder. Being pushed by a knob 730 the piston 724 moves the needles forward through holes 731 in the distal cap 722 forcing the needles to prick perineum 700 situated between scrotum 715 and anus 716 and penetrate prostate 709. An exemplary needle 727 (for simplicity only two needles are shown) has proximal end 726, distal end 728 and electrode 729. The proximal ends of all needles are mounted on the distal surface of the piston 724, electrically insulated from the needles. Through holes on the proximal surface of the piston the needles are electrically connected to wires 731, leading to switchboard circuit 713, used for commutating the high voltage pulsed between separate electrodes or groups of electrodes. The switchboard circuit 713 is coupled to a high voltage pulse generator 109. The needles may be mounted on the piston 724 in two or three rows along concentric circumferences. The electrodes 729, preferentially electrically insulated from the needles, are connected to wires 731, leading to the switchboard circuit 713, with insulated wires disposed inside the hollow needles. The needles in each row may be electrically connected to each other and kept at the same potential during high voltage pulsing. These connections decrease the number of wires that should be placed between the needles and the switchboard circuit 713 and generate an electric field in a predominantly radial direction, the direction that is especially efficient in killing fibro muscular cells positioned radially. The shape of urethral probe 701, its spatial position relatively to the needle cartridge 720 and spacing between the needles are selected to insure that the needles move parallel to the distal part of the urethra and can be placed in the urethra at predetermined radial and longitudinal positions from each other and from the urethra electrode 708. Stated otherwise, the probe member 704 may be configured to include a substantially linear distal end segment that serves to straighten the prostatic urethra when the probe is placed in an operative position in the urethra as shown in the Figure. This distal end segment carries the balloon 705 and the urethral electrode 708. The distal end segment and the needle electrodes 727 each define linear axes that are substantially parallel to each other. With this configuration, then, the needle electrodes 727 may be advanced such that they move substantially parallel to the distal end segment and thus the distal or prostatic urethra. With this configuration of rigid probe, handle, and needle cartridge, the electrodes 729 may be precisely positioned relative to the urethral electrode 708 for application of the electroporation therapy, as will be explained in greater detail with respect to FIG. 8, below.

The relative positioning of the urethral electrode and the needle electrodes in the prostate during treatment is illustrated by FIG. 8. FIG. 8 shows a cross-section of the prostate with all electrodes in place. Numbers 813 and 815 stand for peripheral and central zones of the prostate respectively. Number 812 corresponds to anterior fibro muscular area and 814—for ejaculatory ducts. As can be seen from the FIG. 8, the urethral electrode 808 is placed in the center of the prostate with the needle electrodes 829 positioned around it. A channel 809 connects the distal balloon of the urethral probe and the inflating port located at the proximal end of the probe. Two circumferential rows of needle electrodes are placed concentrically around the urethra. High voltage pulsing applied to the central electrode and any of the rows of electrodes creates a predominantly radially directed electric field. Also, the radial electric field can be created by pulsing the rows of the needle electrodes only, without applying voltage to the central urethral electrode, or it can be created by consecutive pulsing pairs of electrodes positioned at different distances from the urethra along the same radius.

The treatment procedure with a urethra-perineal applicator starts by placing the probe 701 into the urethra 706. Balloon 705 at the distal end of the probe 703 is inflated. Inflated balloon 705 anchors the probe relatively to the urethra and the bladder. Due to selection of the location of electrode 708 on the probe 701, it can be positioned in the urethra at the exact location of the transition zone in the middle of the BPH overgrowth. As the probe 701 is being placed in the urethra, the needles 727 in cartridge 720 stay inactive, hidden in the back position. After the probe 701 is placed and anchored, the scrotum 715 is pulled aside and gently secured at a side and up position to avoid injury by the needles 727 to be advanced. Then the needles 727 are advanced into the forward position. They pierce the perineum 700 and the prostate 729 and deliver the needle electrodes 729 into the treatment positions around the central urethral electrode 708. After placement of all electrodes, the electroporation treatment is performed. Multiple high voltage pulses are delivered to the electrodes to create a radial to the urethra electric field to cause cell death and necrosis of a significant volume of neoplastic tissue, resulting in a relief of BPH symptoms. As the HV pulses are delivered the electrical resistance of the tissue is monitored. The end of the therapy is marked by a significant and stable drop in the resistance of the treated volume of tissue.

Placement of electrodes in the vicinity of prostate using a urethra-perineal applicator does not require ultrasound or other imaging guidance. Precise placement of the needles is provided by high mechanical tolerances of the applicator and high rigidity of the urethral probe. Using the urethra-perineal applicator allows for a short treatment time because it provides treatment in only one position of the electrodes, and does not require repositioning electrodes and multiple manipulation of the applicator.

The urethra-perineal applicator can be used for delivery of electrical energy to the prostate not only in the form of high voltage pulses causing electroporation necrosis, but also in the form of RF energy causing thermal necrosis of BPH.

Different needle electrodes used in the electroporation treatment are shown in FIGS. 9*a, b, c*. FIG. 9*a* shows a one electrode needle adapted for creating electric field normal to the axis of the needle. The needle has a proximal end 901, distal end 902 and a metal hollow body 906. At the distal end 902 the needle is terminated by a sharp metal tip 910 (911), brazed into the hollow body of the needle. A cylindrical electrode 903 is secured on an insulator layer 905 deposited on the needle surface. The electrode 903 (904) is electrically connected to high voltage generator via a wire 907 (908). A version of a similar needle with two electrodes adapted for creating electric field directed along the axis of the needle is shown in the FIG. 9*b*.

In versions 9*a* and 9*b* the sharp tips are electrically separated from the HV electrodes. In version 9*c* the tip is made of an insulating material, like glass, dielectric crystal or ceramics. This feature of the design prevents electric breakdowns and sparking from the tip through the tissue during HV pulsing.

Although preferred embodiments of the invention have been described in some detail, it is understood that obvious variations can be made without departing from the spirit and the scope of the invention as defined by the appended claims.

What is claimed:

1. A method for treating elevated muscle tension on a tubular anatomical structure, the method comprising:
   advancing into the tubular anatomical structure a catheter having at least one electrode; and
   applying, using the advanced electrode, an electrical signal in an amount sufficient to destroy elongate nerve cells that are elevating the muscle tension, wherein the step of applying an electrical signal includes applying a plurality of electrical pulses to cause an electric field in a direction substantially along the length of the elongate nerve cells.

2. A method for treating elevated muscle tension on a tubular anatomical structure, the method comprising:
   advancing into the tubular anatomical structure a catheter having at least one electrode; and
   applying, using the advanced electrode, an electrical signal in an amount sufficient to destroy elongate nerve cells that are elevating the muscle tension, wherein the step of applying includes applying the electrical signal in a direction which is substantially radial to the tubular anatomical structure.

3. A method for treating muscle tension on a tubular anatomical structure, the method comprising:

advancing into the tubular anatomical structure a catheter having at least one electrode;

positioning the electrode of the advanced catheter near a target area containing elongate nerve cells that are elevating the muscle tension; and applying, using the positioned electrode, a plurality of electrical pulses to cause an electric field in an amount sufficient to destroy the elongate nerve cells in the target area, wherein the step of applying includes applying a plurality of electrical pulses to cause the electric field in a direction substantially along the length of the elongate nerve cells.

4. The method of claim 3, wherein:

the electric field is in an amount above an upper limit of electroporation to irreversibly open pores in membranes of the elongate nerve cells, thereby killing the nerve cells in the target area; and each electrical pulse is a rectangular pulse and has a duration of at least 10 microseconds and at most 500 milliseconds.

5. The method of claim 3, wherein:

each electrical pulse has an amplitude of at least 1000 Volts/cm; and the pulses are alternating polarity pulses.

6. A method for treating muscle tension on a tubular anatomical structure, the method comprising:

advancing into the tubular anatomical structure a catheter having at least one electrode;

positioning the electrode of the advanced catheter near a target area containing elongate nerve cells that are elevating the muscle tension; and applying, using the positioned electrode, a plurality of electrical pulses to cause an electric field in an amount sufficient to destroy the elongate nerve cells in the target area, wherein the step of applying includes applying the electrical pulses to cause the electric field in a direction which is substantially radial to the tubular anatomical structure.

7. A method for treating muscle tension on a tubular anatomical structure, the method comprising:

advancing into the tubular anatomical structure a catheter including an expandable member, the expandable member having at least one electrode;

positioning the expandable member of the advanced catheter near a target area containing elongate nerve cells contributing to the muscle tension;

expanding the positioned expandable member; and applying, using the electrode of the expanded expandable member, a plurality of electrical pulses to cause an electric field in an amount sufficient to destroy elongate nerve cells in the target area, wherein the step of applying includes applying a plurality of electrical pulses to cause the electric field in a direction substantially along the length of the elongate nerve cells.

8. A method for treating nerve cells on a tubular anatomical structure, the method comprising:

advancing into the tubular anatomical structure a catheter having at least one electrode; and applying, using the advanced electrode, an electrical energy in an amount sufficient to destroy elongate nerve cells on a tubular anatomical structure, wherein the step of applying an electrical energy includes applying the electrical energy in a direction substantially along the length of the elongate nerve cells.

9. A method for treating nerves on a tubular anatomical structure, the method comprising:

advancing into the tubular anatomical structure a catheter having at least one electrode; and applying, using the advanced electrode, an electrical energy in an amount sufficient to destroy elongate nerve cells on the tubular anatomical structure, wherein the step of applying includes applying the electrical energy in a direction which is substantially radial to the tubular anatomical structure.

10. A method for treating elongate nerve cells on a tubular anatomical structure, the method comprising:

advancing into the tubular anatomical structure a catheter having at least one electrode;

positioning the electrode of the advanced catheter near a target area containing the elongate new cells; and applying, using the positioned electrode, an electrical signal in an amount sufficient to destroy the elongate nerve cells in the target area, wherein the step of applying includes applying the electrical signal in a direction substantially along the length of the elongate nerve cells.

11. A method for treating elongate nerve cells on a tubular anatomical structure, the method comprising:

advancing into the tubular anatomical structure a catheter having at least one electrode;

positioning the electrode of the advanced catheter near a target area containing the elongate nerve cells; and applying, using the positioned electrode, an electrical signal in an amount sufficient to destroy the elongate nerve cells in the target area wherein the step of applying includes applying the electrical signal in a direction which is substantially radial to the tubular anatomical structure.

12. The method of claim 11, wherein:

the positioned electrode comprises a pair of electrodes.

13. The method of claim 12, wherein:

an electric field is created between the pair of electrodes.

14. The method of claim 13, wherein:

the step of applying the electric signal further comprises pulsing the pair of electrodes.

15. The method of claim 11, wherein:

the positioned electrode comprises pairs of electrodes positioned along a common radius.

16. The method of claim 15, wherein:

the step of applying the electric signal further comprises consecutively pulsing the pairs of electrodes.

* * * * *